United States Patent [19]

Vickery

[11] 4,020,844

[45] May 3, 1977

[54] THROAT PACK

[76] Inventor: Ian Malcolm Vickery, 37 Kewstoke Road, Stoke Bishop, Bristol, 9, England

[22] Filed: Mar. 31, 1976

[21] Appl. No.: 672,151

Related U.S. Application Data

[62] Division of Ser. No. 551,714, Feb. 21, 1975, Pat. No. 3,983,877.

[52] U.S. Cl. .......................... 128/303 R; 128/206; 128/296
[51] Int. Cl.² ......................................... A61B 17/24
[58] Field of Search ....... 128/1 R, 206, 296, 303 R, 128/325

[56] References Cited

UNITED STATES PATENTS

| | | | |
|---|---|---|---|
| 2,098,340 | 11/1937 | Henahan | 128/136 |
| 2,179,964 | 11/1939 | Stevens | 128/325 X |
| 2,371,082 | 3/1945 | Vistreich | 128/325 |
| 3,570,494 | 3/1971 | Gottschalk | 128/325 |

Primary Examiner—Channing L. Pace
Attorney, Agent, or Firm—Larson, Taylor & Hinds

[57] ABSTRACT

The present invention provides a throat pack comprising a resilient moulding of polymeric foam material shaped and adapted for insertion into and occlusion of the oro-pharynx or laryngo-pharynx or both.

An exposed region of the foamed material, at least in the anterior surface of the moulding, may be useful in absorbing fluids. One or more safety tapes are incorporated in the pack so as to extend outwards through the mouth.

6 Claims, 7 Drawing Figures

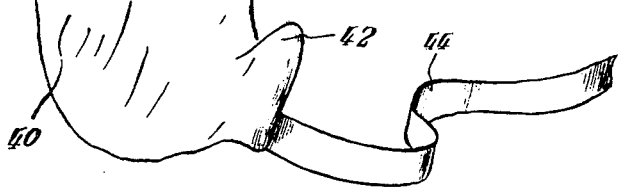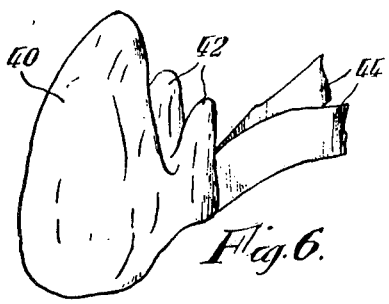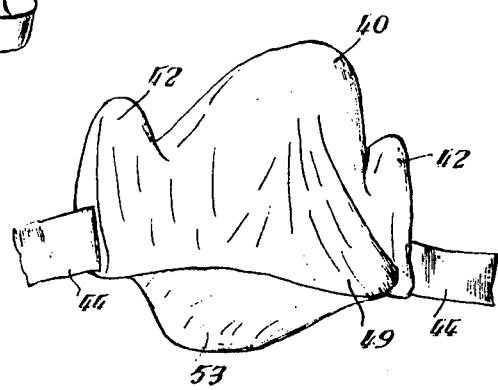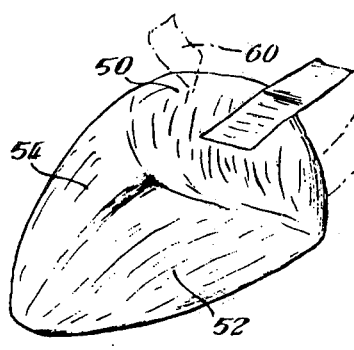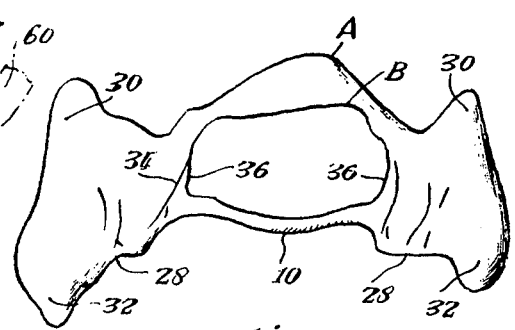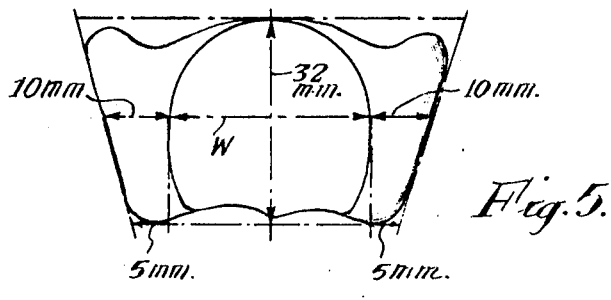

THROAT PACK

This is a division, of application Ser. No. 551,714 filed Feb. 21, 1975, now Pat. No. 3,983,877, Oct. 5, 1976.

FIELD OF THE INVENTION

This invention relates to the field of surgery, and has an object to provide a throat pack, particularly suitable for use in general anaesthesia.

BACKGROUND OF THE INVENTION

The oro-pharynx is that area behind the oral cavity, below the naso-pharynx and above the laryngo-pharynx and the oesophageal entrance. During the administration of some general anaesthetics it is advisable to insert a throat pack to close off part of the oro-pharynx and/or laryngo-pharynx. The purpose of this is to eliminate the passage into the lungs of any harmful foreign material such as blood, saliva, pus, tooth or parts of teeth, and so on. The oro-pharyngeal pack occludes the oral airway and thereby promotes the nasal inhalation of anaesthetic gases. Care must be taken, however, to ensure that the nasal airway is not impaired by a backward displacement either of the tongue or of the soft palate.

DESCRIPTION OF THE PRIOR ART

Hitherto, throat packs have been made up in situ from various materials, such as surgical gauze and wadding. Although these materials are inexpensive and readily available, it is difficult to ensure an effective seal in the irregularly shaped region of the oro-pharynx or laryngo-pharynx. Although the shape of the region is very complicated, the present inventor has, from accurate three-dimensional measurements in a number of subjects, made the surprising discovery that there is remarkably little variation in the size of this space in adults, and that differences only become appreciable in young children.

SUMMARY OF THE INVENTION

The present invention accordingly provides a throat pack comprising a resilient moulding of polymeric foam material shaped and adapted for insertion into and occlusion of the oro-pharynx or laryngo-pharynx or both.

Preferably, the oro-pharyngeal pack is shaped to bear upwardly on the posterior border of the hard palate and downwardly onto the tongue in front of the foramen caecum so as to resist backward displacement of the tongue. The upper surface is desirably shaped so as to avoid appreciable pressure on the soft palate. The lower surface may extend as far back as the foramen caecum, but desirably bears upon the tongue for a distance of up to about 25 mm in front of the foramen caecum. The lateral portions of the moulding preferably comprise lobes adapted to abut against the posterior parts of the buccal sulci and adjacent anterior pillars of the fauces. The anterior part of the moulding preferably has a transverse cross-section appreciably greater than the corresponding oro-pharyngeal section of the patient. In practice, a number of different standard sizes of moulding can be made, for example small, medium and large, and these will suffice to ensure that the moulding will fit all the sections likely to be found in practice with differing compressions on the surrounding tissues.

An exposed region of the foamed material, at least in the anterior surface of the moulding, may be useful in absorbing fluids. One or more safety tapes are incorporated in the pack so as to extend outwards through the mouth. These tapes are preferably incorporated in the posterior part of the pack, and extend from any convenient point or points. For example, by extending from the sides the tapes can be used to hold the pack in a compact form during insertion and then be released to allow the pack to occlude the oro-pharynx.

BRIEF DESCRIPTION OF THE DRAWINGS

In order that the invention may be more clearly understood, two embodiments will now be described with reference to the accompanying drawings, wherein:

FIG. 1 shows a perspective view from above of the posterior part of a moulding of an oro-pharyngeal throat pack, FIG. 2 shows a perspective view from below of the anterior part of the moulding, FIG. 4 shows a frontal view of the oro-pharyngeal region of the mouth, FIG. 5 shows a representation of the frontal view of the pack showing the varying size of the inlet, FIG. 6 shows a perspective view of the pack compressed for insertion, and FIG. 7 shows a perspective view from below of a laryngo-pharyngeal throat pack.

Figure 3:
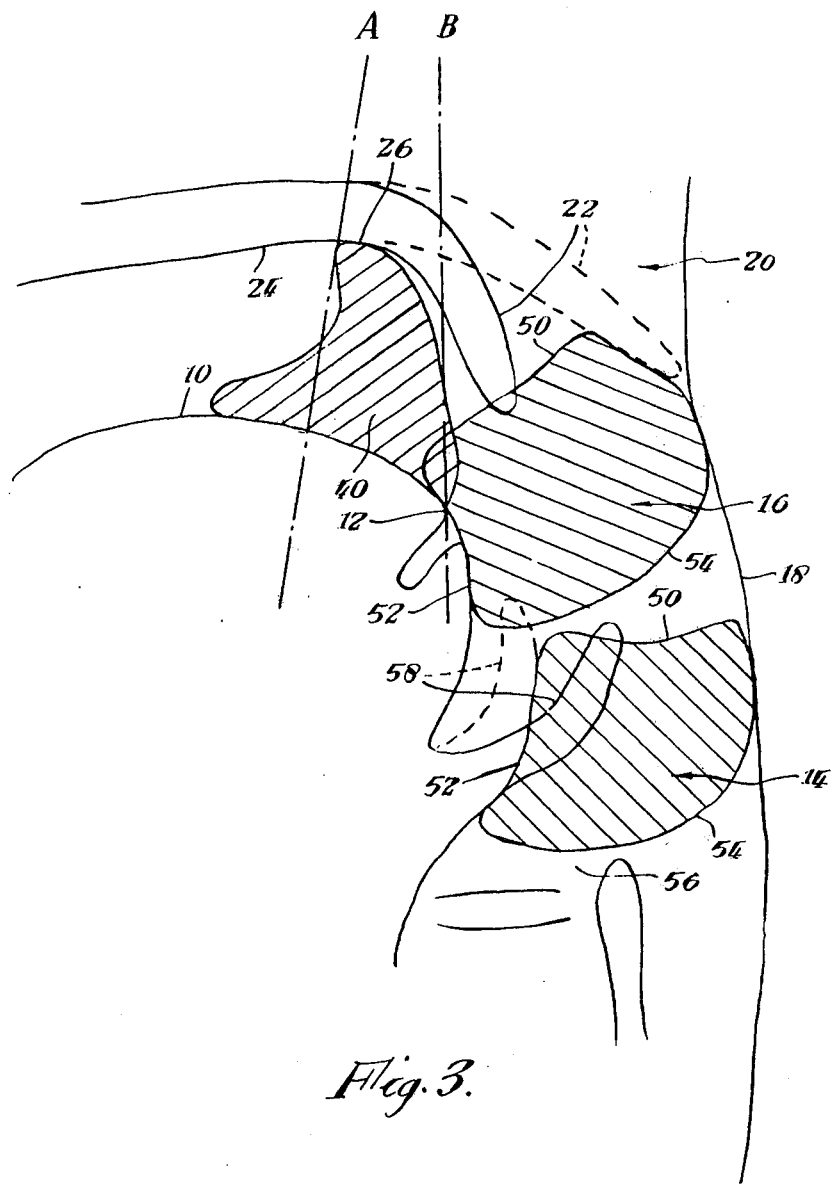
FIG. 3 shows a sagittal section through the mouth, pharynx, larynx and oesophagus with positions of throat packs indicated.

Referring to the drawings; oro-pharyngeal/laryngo-pharyngeal moulds were taken from a series of patients of varying ages, and accurate three-dimensional measurements were made giving a range of figures. As previously indicated, it was found that there was remarkably little variation in adults, and that the differences only became appreciable in young children. A typical oro-pharyngeal shape is indicated by FIGS. 3 and 4. In these Figures, the various anatomical regions are indicated as follows: the tongue 10, foramen caecum 12, laryngo-pharynx 14, oro-pharynx 16, posterior pharyngeal wall 18, naso-pharynx 20, soft palate 22, hard palate 24, posterior border of hard palate 26, retro-molar pads 28, buccal sulci 30, lower buccal sulci 32, anterior pillars of fauces 34 and posterior pillars of fauces 36. Two cross-sections A and B are indicated in FIG. 3, each at right angles to the sagittal section, B being a coronal section through the foramen caecum, and A being somewhat inclined to a coronal section and passing through the posterior border of the hard palate and a point on the tongue about 25 mm in front of the foramen caecum. The shape of the sections at A and B are indicated in FIG. 4.

In designing the oro-pharyngeal throat pack, the object was to provide a peripheral seal with the surrounding tissue in the region of section A. Thus, the pack, which is shown in FIGS. 1 and 2, comprises a central portion 40 and two lateral lobes 42. The maximum oro-pharyngeal dimensions likely to be encountered in clinical practice were estimated from measurements on the experimentally obtained moulds. From this three representative master mould sizes were selected. FIG. 5 shows the representation of the frontal view of the oro-pharyngeal region with the variable width of the inlet represented as W. The three sizes for W were selected as follows: Large W = 50 mm, medium W = 42 mm, and small W = 34 mm; giving total widths of the regions as 70 mm, 62 mm and 54 mm respectively. With the deformability of the material of the throat pack, it was considered that packs having these frontal dimensions would suit any section likely to be encountered in practice, and would provide appreciable overlap between adjacent sizes so that in any situation where there might be uncertainty as to correct size pack, either of the two possible sizes would suffice. The given dimensions are at least 10 mm larger than any of the dimensions found in the moulds taken from patients. The important factor is to close the inlet without bearing upon the soft palate. It was found that, using a constant vertical dimension of about 32 mm for the pack, the pressure on the pack between the tongue and hard palate compressed the pack vertically and distorted it laterally, so that provided dimension W was not too great the vertical distortion of the pack would not result in pressure on the soft palate.

As shown in FIG. 3, the central section 40 of the mould at the top bears upon the posterior border of the hard palate and then curves downwardly clear of the soft palate to the region of the foramen caecum, and then forwardly about 25 mm to the plane A. The lateral portions of the master mould were designed so as to extend from the posterior part of the tongue onto the retro-molar pad areas, upwardly over the most posterior buccal sulci and anterior pillars of the fauces, and forward to the junction of the hard and soft palates. The anterior surface of the mould was shaped so as to provide a somewhat concave surface as indicated in FIG. 3. This was to give maximum operating space within the mouth.

From these three master moulds there were made mouldings in resilient foamed plastics material. Safety tapes 44 were incorporated into the posterior part of the mouldings so as to project from the sides thereof, as indicated in FIGS. 1 and 2. These tapes project from the mouth when the pack is in position, to enable the pack to be readily withdrawn. They also can be used to draw together the lobes 42 of the moulding, as shown in FIG. 6, to hold the moulding in a compact form suitable for insertion.

The sagittal plane contour of the moulding is such that by allowing its upper surface to abut against the hard palate near the soft palate junction its lower surface holds the tongue forward. The oversize anterior section of the moulding not only ensures a continuous seal, but also assists in providing the necessary downward and forward pressure on the tongue. The posterior portion of the central region 40 is curved down clear of the soft palate in the region of the foramen caecum to avoid pushing the soft palate towards the naso-pharynx, but the precise form of this region is probably not critical. The lateral lobes 42 abut the most posterior buccal sulci and adjacent anterior pillars of the fauces, and this assists in maintaining the forward displacement of the tongue. Further stability is given by the rapid narrowing of the anterior part of the oro-pharynx.

The pack can be formed as a simple foam moulding, but is preferably provided with a very thin outer moisture-impermeable layer, at least on its posterior surfaces. This may be provided by applying a coating of a suitable composition, such as polyurethane. It may be desirable to keep the foam exposed on the anterior surface to assist in absorption of fluid.

As well as in general anaesthesia, the pack might be useful in local anaesthesia where certain sedation techniques ae being used.

The second form of pack shown in FIG. 6 may be moulded from foamed plastics material with an impermeable layer on its posterior surface. The anterior surface 50 is somewhat concave, as in the previous embodiment, the inferior surface 52 is generally triangular and very slightly concave, and the superior posterior and lateral portions 54 form one smooth convex surface. This pack is intended to occlude the oropharyngeal inlet at any position from the foramen caecum backwards and downwards to and including the laryngeal inlet 56, the latter position being indicated in FIG. 3, where the surface 52 lies over the epiglottis 58. Two possible positions are shown in FIG. 3. A tape 60 is provided to assist in removing the pack. A pair of lateral tapes could be provided instead, as in the previous embodiment. Its general shape is conical for ease of insertion, and is about 50 mm long. The cross-section of anterior surface 50 was taken from the sections of the inlet B in the various experimental moulds. The anterior surface, of about 60 mm wide and 35 mm high, was dimensioned so as to be 5-10 mm larger than any inlet dimension found in the experimental moulds. Only one size of pack is required, since the need to avoid pressure on the soft palate is not present.

Since the pack of FIG. 7 occludes the nasal airway, it will be used in conjunction with an endotracheal tube, whereas the pack of the first embodiment does not occlude the airway and is therefore particularly suitable, for example for dental surgery where and endotracheal tube is not neccessarily used.

Various polymeric materials may be employed for the pack, such as polyurethane, natural or synthetic rubber, for example silicone elastomer. Essentially the material has to be resiliently compressible.

It will be appreciated that, because of the highly compressible nature of the foam material, the shape of the packs when installed differ substantially from the initial shape prior to insertion, as can be seen from FIG. 3. The important point in designing these packs, however, is to ensure a complete seal around the region to be occluded, and since the shapes of these regions are generally highly tortuous and vary a good deal between patients, it will be understood that a throat pack to cover a range of patients will not have a shape which corresponds closely to the section of any one patient.

The positional designation of the surfaces and parts of the throat packs refers to their position with respect to the body when the throat pack is introduced into the mouth. The positions of these surfaces in the laryngopharyngeal throat pack will, of course, alter as it passes toward the laryngeal inlet. For example, the anterior surface becomes the anterior-superior and then superior surface.

I claim:

1. A laryngo-pharyngeal throat pack having an anterior portion for occluding under compression the laryngo-pharyngeal passage, and a generally tapering posterior portion, the occluding section having a smoothly convex superior, posterior and lateral surface merging with a generally flat interior surface, the inferior surface tapering rearwardly to have a generally triangular outline, the superior, posterior and lateral surface sloping rearwardly to merge with the inferior surface providing a semi-conical tapering shape to the pack rearwardly of the occluding section.

2. A laryngo-pharyngeal throat pack according to claim 1 having a somewhat concave anterior surface.

3. A larygo-pharyngeal throat pack according to claim 1 wherein the molding is provided with a moisture impermeable layer on at least its posterior surfaces.

4. A throat pack according to claim 1 wherein the molding is provided with one or more tapes to assist in withdrawal of the pack.

5. throat pack according to claim 4 wherein lateral tapes are provided to allow the side portions of the pack to be drawn together for insertion of the pack.

6. A method of occluding the laryngo-pharyngeal passage, which comprises inserting into the selected regions through the mouth of a patient a throat pack as claimed in claim 1 so that the pack seats in said region under continuous peripheral compression around a cross-section of said region.

* * * * *